US011346852B2

(12) United States Patent
Schwoebel

(10) Patent No.: US 11,346,852 B2
(45) Date of Patent: May 31, 2022

(54) METHOD AND SYSTEM FOR QUALITY EVALUATION OF A HANDHELD ANALYTICAL DEVICE

(71) Applicant: Roche Diabetes Care, Inc., Indianapolis, IN (US)

(72) Inventor: Wolfgang Schwoebel, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 193 days.

(21) Appl. No.: 16/867,303

(22) Filed: May 5, 2020

(65) Prior Publication Data

US 2020/0264202 A1 Aug. 20, 2020

Related U.S. Application Data

(63) Continuation of application No. 16/109,309, filed on Aug. 22, 2018, now Pat. No. 10,684,299, which is a (Continued)

(30) Foreign Application Priority Data

Feb. 25, 2016 (EP) ..................................... 16157282

(51) Int. Cl.
*G01N 35/00* (2006.01)
*G01N 27/327* (2006.01)
(Continued)

(52) U.S. Cl.
CPC ........ *G01N 35/0099* (2013.01); *B25J 9/0087* (2013.01); *B25J 9/1664* (2013.01); (Continued)

(58) Field of Classification Search
None
See application file for complete search history.

(56) References Cited

U.S. PATENT DOCUMENTS

2006/0222567 A1* 10/2006 Kloepfer .............. G01N 33/558
422/68.1
2009/0265035 A1* 10/2009 Jenkinson .............. B25J 9/0096
901/14
(Continued)

FOREIGN PATENT DOCUMENTS

CN 101581685 A 11/2009
CN 102067151 A 5/2011
(Continued)

OTHER PUBLICATIONS

U.S. Department of Health and Human Services, Applying Human Factors and Usability Engineering to Medical Devices: Guidance for Industry and Food and Drug Administrative Staff, Feb. 3, 2016, pp. 1-45.
(Continued)

*Primary Examiner* — Matthew D Krcha
(74) *Attorney, Agent, or Firm* — Bose McKinney & Evans LLP

(57) ABSTRACT

This disclosure concerns a method and a system for quality evaluation of a handheld analytical device, wherein the device is operable by a human user in a sequence of handling steps to test an analyte in a sample fluid applied on a test element, the method comprising the steps of (a) programming a handling cycle for a robot having at least one robot arm in order to mimic the sequence of handling steps, (b) operating the device in at least one handling cycle by means of the robot, (c) monitoring the operation in step (b) by a control unit to evaluate at least one parameter influencing the quality of the device.

7 Claims, 3 Drawing Sheets

Related U.S. Application Data continuation of application No. PCT/EP2017/054427, filed on Feb. 25, 2017, which is a continuation of application No. 15/053,074, filed on Feb. 25, 2016, now abandoned.

(51) Int. Cl.
*B25J 9/00* (2006.01)
*B25J 11/00* (2006.01)
*B25J 9/16* (2006.01)
*G01N 33/66* (2006.01)

(52) U.S. Cl.
CPC .......... *B25J 11/00* (2013.01); *G01N 27/3273* (2013.01); *G01N 33/66* (2013.01); *G01N 35/00613* (2013.01); *G01N 35/00722* (2013.01); *G01N 2035/0091* (2013.01)

(56) References Cited

U.S. PATENT DOCUMENTS

| | | |
|---|---|---|
| 2013/0065797 A1 | 3/2013 | Silbert et al. |
| 2013/0288355 A1 | 10/2013 | DeWitte et al. |
| 2015/0355131 A1 | 12/2015 | Elder et al. |
| 2016/0016171 A1 | 1/2016 | Goel |

FOREIGN PATENT DOCUMENTS

| | | |
|---|---|---|
| CN | 103331506 A | 10/2013 |
| CN | 103370627 A | 10/2013 |
| CN | 105142789 A | 12/2015 |
| CN | 105164508 A | 12/2015 |
| DE | 101 61 470 A1 | 6/2003 |
| DE | 10 2005 047 204 A1 | 4/2007 |
| JP | 2014-526687 A | 10/2014 |
| KR | 10-2011-0010094 A | 1/2011 |
| WO | WO 2006/043873 A1 | 4/2006 |
| WO | WO 2009/129526 A1 | 10/2009 |

OTHER PUBLICATIONS

International Search Report and Written Opinion, PCT/EP2017/054427, dated Jun. 8, 2017, 8 pages.

Berger et al., Intelligent PC-Based User Control Interface for On-Line Correction of Robot Programs, 7th International Conference on Control, Automation, Robotics and Vision, 2002, pp. 276-281.

Berger et al., Intelligent Production Monitoring and Control for Mass Customization of Automated Manufacturing Cells in the Automotive Industry, 7th International Conference on Control, Automation, Robotics and Vision, Proceedings of the 4th World Conference on Mass Customization and Personalization, 2007, 8 pgs.

\* cited by examiner

METHOD AND SYSTEM FOR QUALITY EVALUATION OF A HANDHELD ANALYTICAL DEVICE

RELATED APPLICATIONS

This application is a continuation of Ser. No. 16/109,309, filed Aug. 22, 2018, which is a continuation of PCT/EP2017/054427, filed Feb. 25, 2017, which claims priority to EP 16 157 282.1, filed Feb. 25, 2016, and which also claims priority to U.S. patent application Ser. No. 15/053,074, filed Feb. 25, 2016, the entire disclosures of all of which are hereby incorporated herein by reference.

BACKGROUND

This disclosure concerns a method for quality evaluation of a handheld analytical device, specifically a blood glucose meter, wherein the device is operable by a human user in a sequence of handling steps to test an analyte in a sample fluid applied on a test element. This disclosure further concerns a system for quality evaluation of such a handheld or hand-operated analytical device.

A typical operation of a handheld blood glucose meter may include a sequence of handling steps like producing a blood sample by lancing a body part, applying the blood sample onto a disposable test element and measuring the test element in the handheld meter in order to obtain a measurement result on the spot. Such analytical devices are usually operated by patients under various conditions and state of health. Then, the inherent problem exists that a lot of individual variations may influence the reproducibility of the diagnostic test, which make it difficult to investigate and identify possible influencing parameters on the quality of the device. For example, when handheld blood glucose monitoring devices are used, variations may arise from "human factors" such as timing when applying the sample, force exertion, impurities on the skin and so on.

SUMMARY

This disclosure further improves known methods and systems for quality evaluation and provides enhanced reproducibility in "human factor" studies in an efficient way.

This disclosure is based on the idea of using an appropriately programmed robot. Thus, it is proposed according to this disclosure that a method for quality evaluation of a handheld analytical device, specifically a blood glucose meter, comprises the steps of
  (a) programming a handling cycle for a robot having at least one robot arm in order to mimic a sequence of handling steps of a human user,
  (b) operating the device in at least one handling cycle by means of the robot,
  (c) monitoring the operation in step (b) by a control unit to evaluate at least one parameter influencing the quality of the device.

Thereby it is possible to investigate different test scenarios in a defined manner and to identify the influences of possible flawed human interactions on the final measurement result. In particular, by providing an automated handling cycle for the robot to be carried out with specific commands, actions and/or steps to closely imitate or mimic a user behavior, standardized and highly reproducible human factor studies are enabled.

Advantageously, monitoring the operation of the device comprises obtaining a test result with the device. Thus, inspection results can be achieved in a realistic and efficient way.

Another improvement in this connection provides that evaluating a parameter influencing the quality of the device comprises determining a measurement accuracy of the device.

It is also preferred that an operating condition of the robot is modified in a plurality of handling cycles in order to identify an influence on the quality or accuracy of the device.

A further preferred embodiment comprises adapting or modifying one or more handling cycles to simulate differences in user handling and evaluating an influencing parameter resulting therefrom.

In particular, it is advantageous by adapting or modifying one or more handling cycles to account for any forms of deviant user handling which is due to or derived from an impairment or illness of the user. Specifically, an impairment of perception and cognitive abilities or an illness such as a tremor, trembling or shaking (e.g. in connection with diseases like Parkinson or Alzheimer) may be accounted for.

In this connection, it is also advantageous to reproduce a user's impairment or illness by adapting the handling cycle in a number of degrees of freedom of the robot movement, e.g. in spatial direction, amplitude, velocity and frequency of an oscillation or deflection of the robot (arm and/or artificial finger).

According to a particularly preferred embodiment, an artificial finger on the robot arm is used to apply sample fluid to a test element, specifically whole blood or artificial blood. The use of such an artificial finger enables mimicking of various factors of the user handling of a handheld analytical device such as a blood glucose meter very close to reality.

Preferably, the handling cycle comprises moving the artificial finger with a predefined orientation and/or force towards a test element. Such movements can be carried out by the robot with high precision and a maximum of repeat accuracy.

In order to simulate the sampling of blood, the handling cycle preferably comprises loading the artificial finger with sample fluid by means of a fluid supply arranged within the artificial finger or by means of a pipette.

For further improvement of the inspection procedure it is advantageous when the artificial finger is provided with a property similar to a human finger, in particular at least one of a predefined elasticity, skin friction, surface contamination and color.

For imitation of human manipulation of a handheld instrument, the handling cycle preferably comprises grabbing the device with a free receiving end of the robot arm.

Another improvement in this direction is achieved when the robot is provided with one or two robot arms and the handling cycle provides for simulation of at least one of right-handed, left-handed, single-handed and two-handed use of the device.

In order to allow complex and highly precise handling operations, it is preferred to make each robot arm rotatable around at least five different axes provided in articulated joints distributed along the length of the robot arm.

According to a particular embodiment the handling cycle comprises continuously carrying the device by the robot arm or depositing the device intermittently within the reach of the robot arm.

According to a further preferred implementation, a graphical user interface is used for simplified programming of the handling cycle as a chain of preprogrammed modules which define elementary movements of the robot. This allows establishing, by way of combining graphical symbols which represent the preprogrammed modules, a robotically guided inspection procedure even for personnel without profound knowledge in the field of robotics.

A further improvement in this direction is that movement paths of the robot can be modified by re-arranging graphical symbols on a display which represent the preprogrammed modules.

A still further improvement comprises simulating the handling cycle by running the chain of modules on a computer system separate from the robot.

Another aspect of this disclosure concerns a system for quality evaluation of a handheld analytical device, specifically a blood glucose meter, which is operable by a human user in a sequence of handling steps to test an analyte in a sample fluid applied on a test element, the system further comprising a robot which is programmed to mimic the sequence of handling steps in an automated handling cycle, and a control unit adapted for monitoring operation of the device in one or more handling cycles to evaluate at least one parameter influencing the quality of the device. Such a system allows carrying out the method as described above and simulating patient behavior close to reality in human factor studies.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
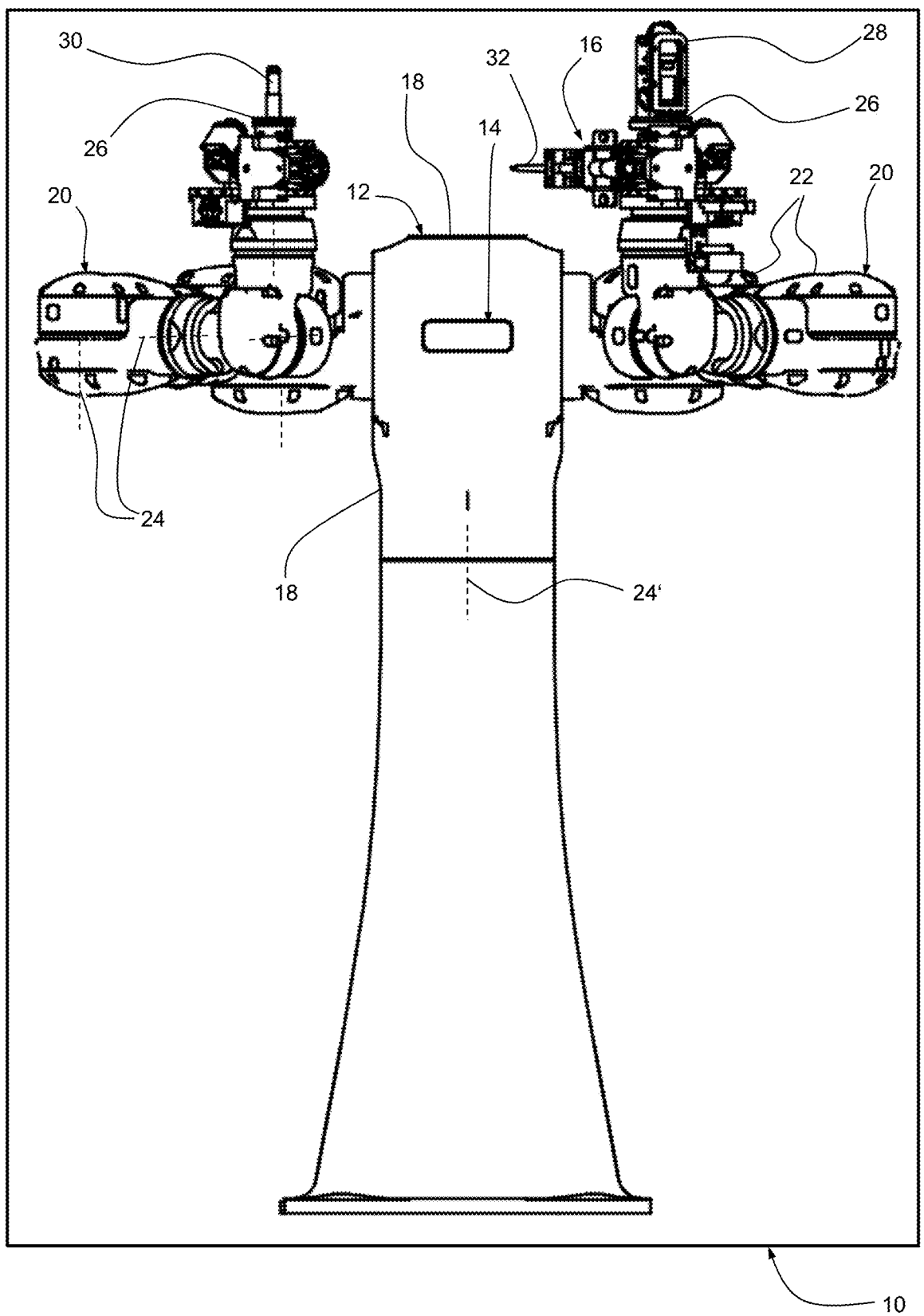
FIG. 1 is a front view of an automated laboratory including a robot for quality evaluation of a blood glucose meter.

FIG. 1 shows a robot cell 10 including a robot 12, a control unit 14 and testing equipment 16 such as diagnostic devices, auxiliary instruments and samples. The robot 12 comprises a robot base 18 and two robot arms 20 extending in opposite directions from the base. Each robot arm 20 consists of several links 22 which are connected by articulated joints for rotation around respective axes 24. The distal link includes a grabber 26 to manipulate a handheld blood glucose meter 28 and an artificial finger 30 as well as other equipment such as a pipette 32.

The robot 12 has at least fifteen axes of rotation including the pivoting axis 24' of its base 18. By defined rotational movements the robot arms 20 follow desired trajectories within the robot cell 10. The robot arms 20 are independently movable under control of a robot program running on the control unit 14 for performing a predefined handling cycle. The handling cycle mimics a sequence of handling steps which are carried out by a human user when operating the blood glucose meter 28. In this way, the quality or design of a diagnostic instrument can be evaluated or inspected under reproducible conditions without human interference.

Figure 2:
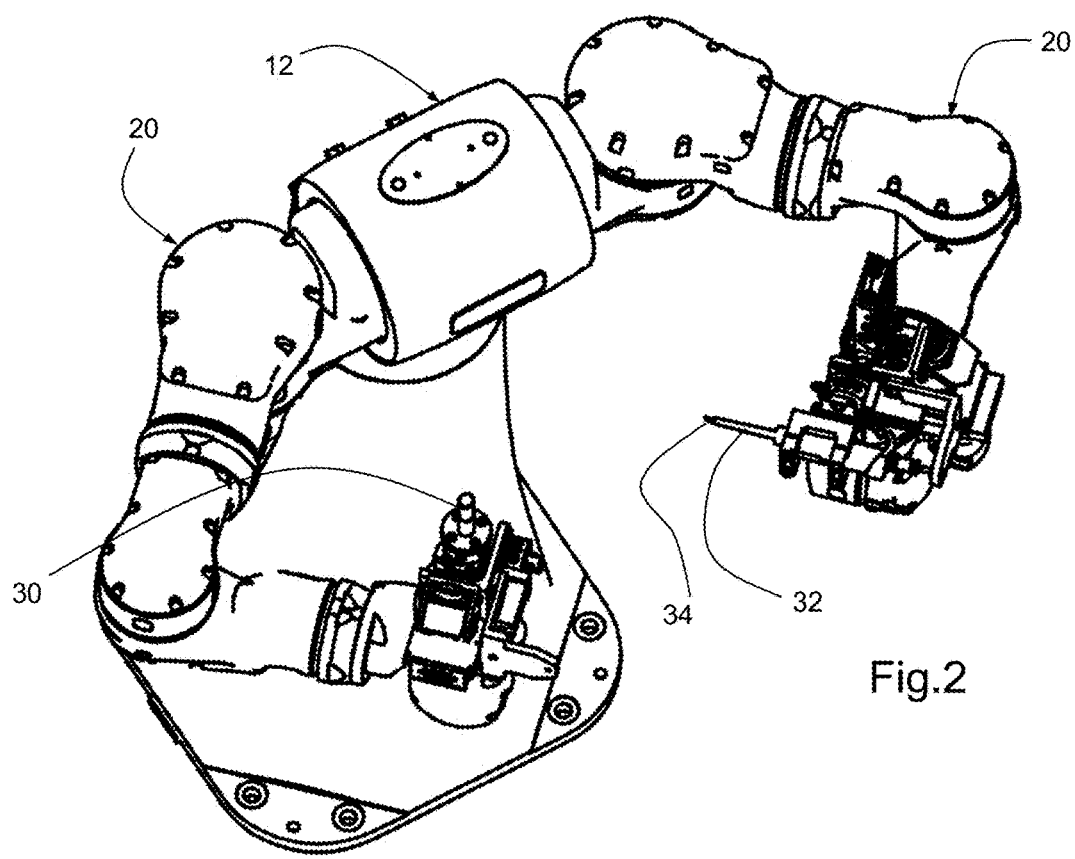
FIG. 2 is a perspective view of the robot when pipetting blood onto an artificial finger.

As illustrated in FIG. 2, the handling cycle comprises loading the artificial finger 30 by means of the pipette 32 with a droplet of blood 34 as sample fluid. Such a step imitates sampling of blood by lancing the finger pad of a human. The pipette 32 may be handled while the meter 28 is still received on the distal end of the same robot arm 20. It is also conceivable to deposit the meter 28 or other equipment intermittently in a rack of the robot cell 10.

Figure 3:
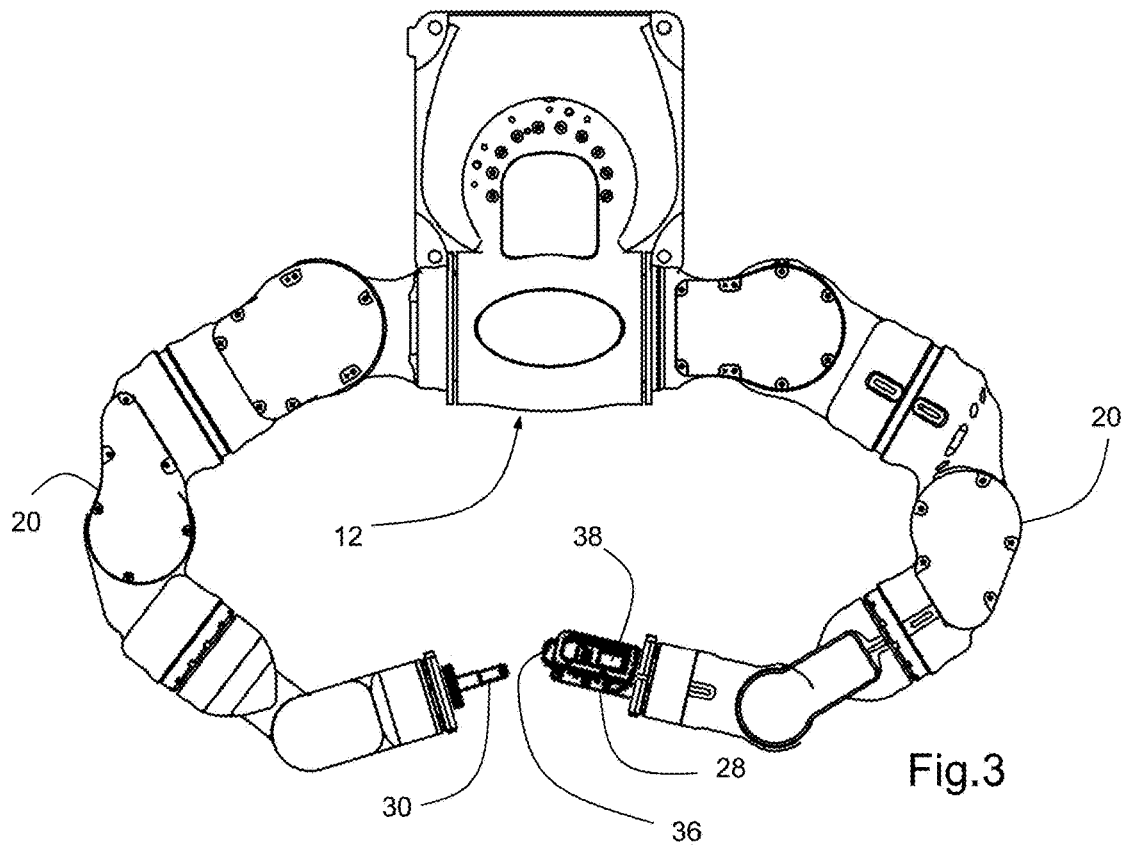
FIG. 3 is a top view of the robot when moving the artificial finger towards the blood glucose meter.

As further apparent from FIG. 3, a next step of the handling cycle comprises moving the artificial finger 30 towards a test element 36 for sample application. The test element 36 may be provided as a section of a test tape which is inserted in the form of a tape cassette into the meter 28.

When operated by a human user, the meter 28 is held in one hand, while a finger of the other hand is pressed against a tip which deflects the test tape. The test element 36 is optically scanned by a photometric measuring unit inside the meter 28, and the measuring result is indicated on a display 38.

In order to specifically mimic the blood application, the artificial finger 30 may be provided with properties similar to a human finger, in particular a corresponding geometry, elasticity and skin friction. Such a replication can be achieved by a steel core covered by several silicone layers of different rigidity. More generally, artificial finger 30 has a hard core replicating human bone covered by one or more softer outer layers replicating human skin.

It is also possible to investigate the influence of a surface contamination of the artificial finger 30 on the measurement accuracy of the meter 28. As a further influencing parameter, the mechanics of the sample application may be further examined, for example by varying the orientation or contact pressure of the artificial finger 30 when contacting the test element 36 in different cycles. For a realistic interaction, the artificial finger 30 should have a sufficient length and a curved surface contour on the end segment. In this context, it is also advantageous that the robot 12 is provided with two robot arms 20 in order to simulate the user behavior, e.g. a right- or left-handed use.

The influence of a parameter or factor on the operation of the meter 28 can be directly monitored by recording a measured test result, namely, a glucose reading. For example, when performing a series of handling cycles, the contact pressure of the artificial finger 30 may be varied, and the measuring results may be recorded by a camera connected to the control unit 14 for capturing an image of the display 38. The variance of the glucose readings may then provide information on a possible influence of the contact pressure. The control unit 14 allows to precisely carry out such a quality evaluation without human user interaction and interference.

Figure 4:
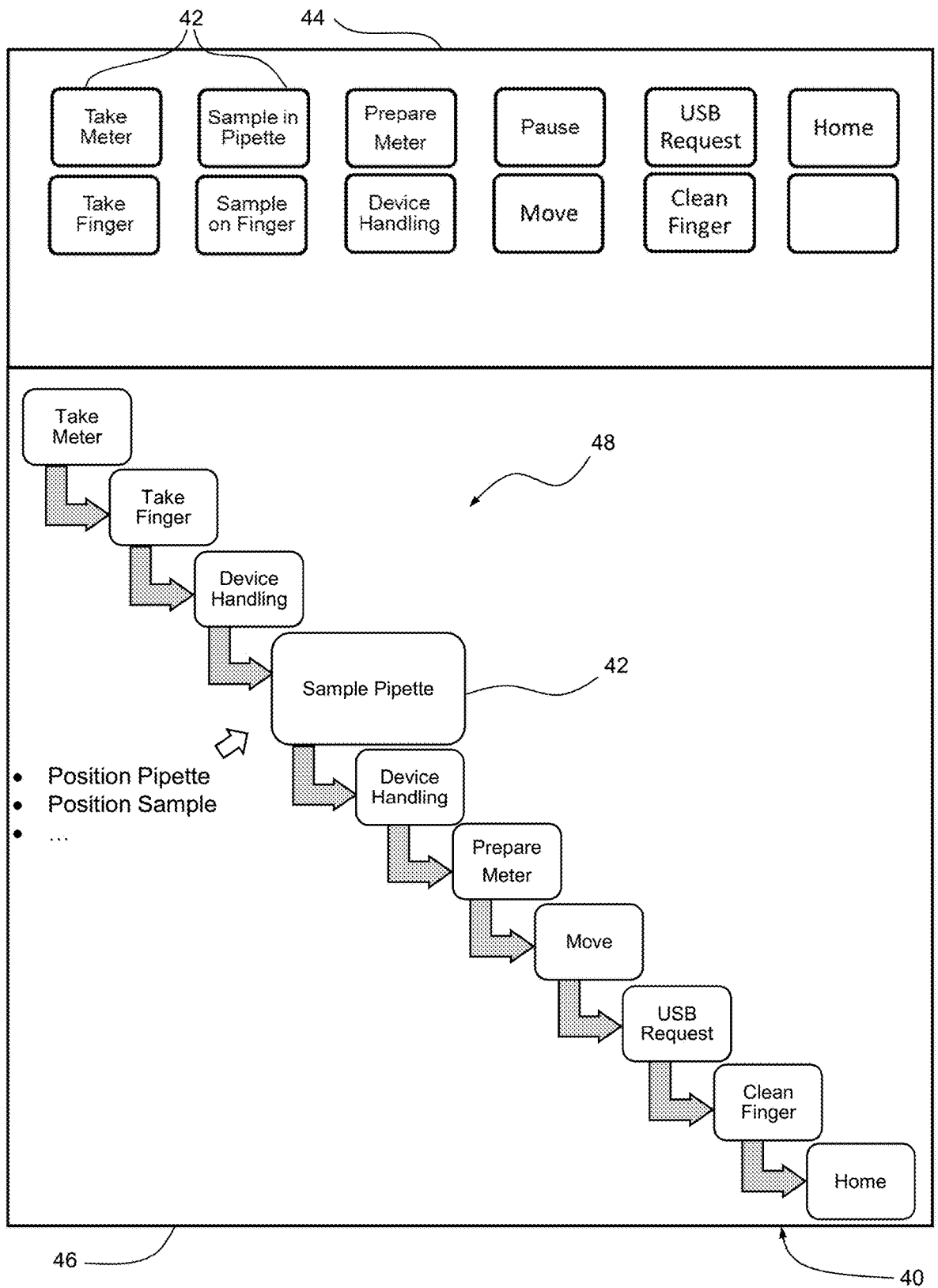
FIG. 4 shows a graphical user interface for programming a handling cycle for the robot.

FIG. 4 shows a graphical user interface (GUI) 40 for simplified programming of a complex handling cycle for the robot 12. The GUI 40 may be installed on a computer system separate from the robot 12. It contains a compilation of preprogrammed modules which define elementary movements or actions of the robot 12 and which are represented by graphical symbols 42 in a first section of a display 44. The computer system allows the operator to drag and drop the symbols 42 into a second display section 46 in order to define a chain 48 of modules for implementation of a corresponding step in the handling cycle of the robot 12.

The user may point to a specific module in the chain 48, e.g., by means of a mouse pointer, whereby a list of predefined variables opens and allows to input or to modify certain values. It is also possible to copy and paste a module chain 48 for definition of a further step or element in the handling cycle. In order to modify movement paths, the GUI 40 provides to re-arrange a selected symbol 42 and to assign desired values to displayed variables.

Advantageously, the computer system allows to simulate the handling cycle separate from the robot 12, so as to avoid collisions or damage of equipment. Then, the generated robot program can be loaded into the control unit 14. In this way, it is possible for an operator to run the robot cell 10 even without sound knowledge of automation, informatics and/or robot programming.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A system for quality evaluation, comprising:
   a handheld analytical device operable by a human user in a sequence of handling steps to test an analyte in a sample fluid applied on a test element;
   a robot programmed to mimic the sequence of handling steps in an automated handling cycle, the robot having an artificial finger, wherein the robot is further programmed to use the artificial finger to mimic various factors of a user handling the handheld analytical device to perform a self test; and
   a control unit programmed to monitor operation of the device in one or more handling cycles to evaluate at least one parameter influencing the quality of the device.

2. The system of claim 1, wherein the analytical device is a glucose meter and the analyte is glucose.

3. The system of claim 1, wherein the artificial finger is configured to apply sample fluid to a test element.

4. A system for quality evaluation, comprising:
   a handheld analytical device operable by a human user in a sequence of handling steps to test an analyte in a sample fluid applied on a test element;
   a robot programmed to mimic the sequence of handling steps in an automated handling cycle, the robot having an artificial finger, wherein the robot is further programmed to use the artificial finger to apply sample fluid to a test element; and
   a control unit programmed to monitor operation of the device in one or more handling cycles to evaluate at least one parameter influencing the quality of the device.

5. The system of claim 4, wherein the analytical device is a glucose meter and the analyte is glucose.

6. A system for quality evaluation, comprising:
   a handheld analytical device operable by a human user in a sequence of handling steps to test an analyte in a sample fluid applied on a test element;
   a robot programmed to mimic the sequence of handling steps in an automated handling cycle which includes adapting the handling cycle in a number of degrees of freedom of robot movement to thereby reproduce a user's impairment or illness; and
   a control unit programmed to monitor operation of the device in one or more handling cycles to evaluate at least one parameter influencing the quality of the device.

7. The system of claim 6 wherein the analytical device is a glucose meter and the analyte is glucose.

\* \* \* \* \*